(12) United States Patent
Inokuchi et al.

(10) Patent No.: US 8,133,586 B2
(45) Date of Patent: *Mar. 13, 2012

(54) SILICONE MICROPARTICLES COMPRISING SILICONE ELASTOMER SPHERICAL MICROPARTICLES COATED WITH POLYORGANOSILSESQUIOXANE, AND METHOD OF PRODUCING SAME

(75) Inventors: Yoshinori Inokuchi, Annaka (JP); Ryuji Horiguchi, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 154 days.

This patent is subject to a terminal disclaimer.

(21) Appl. No.: 12/609,429

(22) Filed: Oct. 30, 2009

(65) Prior Publication Data
US 2010/0112074 A1  May 6, 2010

(30) Foreign Application Priority Data
Oct. 31, 2008  (JP) .................................. 2008-281527

(51) Int. Cl.
*B32B 5/66* (2006.01)
(52) U.S. Cl. ......... 428/403; 428/406; 428/407; 427/212
(58) Field of Classification Search .................. 428/403, 428/406, 407; 427/212
See application file for complete search history.

(56) References Cited

U.S. PATENT DOCUMENTS
5,538,793 A * 7/1996 Inokuchi et al. .............. 428/407

FOREIGN PATENT DOCUMENTS

| | | | |
|---|---|---|---|
| EP | 0 958 805 | A2 | 11/1999 |
| EP | 0 958 805 | A3 | 11/1999 |
| EP | 0958805 | * | 11/1999 |
| EP | 1 582 203 | A1 | 10/2005 |
| EP | 1582203 | * | 10/2005 |
| EP | 1 777 278 | A1 | 4/2007 |
| EP | 1777278 | * | 4/2007 |

OTHER PUBLICATIONS

U.S. Appl. No. 12/609,524, filed Oct. 30, 2009, Inokuchi, et al.

* cited by examiner

*Primary Examiner* — Leszek Kiliman
(74) *Attorney, Agent, or Firm* — Oblon, Spivak, McClelland, Maier & Neustadt, L.L.P.

(57) ABSTRACT

Provided are silicone microparticles including 100 parts by mass of silicone elastomer spherical microparticles having a volume average particle diameter within a range from 0.1 to 100 μm, and 0.5 to 25 parts by mass of a polyorganosilsesquioxane that coats the surface of the silicone elastomer spherical microparticles, in which the silicone elastomer is capable of absorbing not less than 200 parts by mass of a polymethylsiloxane having a viscosity at 25° C. of not more than 10 mm$^2$/s per 100 parts by mass of the silicone elastomer. These silicone microparticles are capable of absorbing a large amount of the above types of polymethylsiloxanes, which represent low-viscosity silicones, and can therefore suppress the greasiness, stickiness, and oily film feeling of cosmetic materials containing this type of polymethylsiloxane. The silicone microparticles can be produced by hydrolyzing and condensing an organotrialkoxysilane in a water medium, in the presence of the above silicone elastomer spherical microparticles and an alkaline material, thereby coating the surface of the silicone elastomer spherical microparticles with a polyorganosilsesquioxane.

19 Claims, No Drawings

SILICONE MICROPARTICLES COMPRISING SILICONE ELASTOMER SPHERICAL MICROPARTICLES COATED WITH POLYORGANOSILSESQUIOXANE, AND METHOD OF PRODUCING SAME

BACKGROUND OF THE INVENTION

1. Field of the Invention

The present invention relates to silicone microparticles comprising silicone elastomer spherical microparticles coated with a polyorganosilsesquioxane which are able to absorb polymethylsiloxanes having a viscosity of not more than 10 mm$^2$/s, and also relates to a method of producing such silicone microparticles.

2. Description of the Prior Art

Cosmetic materials containing an added low-viscosity silicone are used to impart softness and smoothness to the skin, thus providing an emollient effect, but these types of cosmetic materials suffer from the unavoidable drawbacks of greasiness, stickiness, and an oily film feeling.

Conventionally, silicone particles have been used to impart cosmetic materials with favorable feelings during use, such as a feeling of silkiness or smoothness, and also to impart improved extensibility. In particular, silicone microparticles comprising spherical microparticles of a silicone rubber coated with a polyorganosilsesquioxane (see Patent Document 1) have a soft feel, are non-cohesive, and exhibit excellent dispersibility, and are therefore used in a wide variety of cosmetic materials. However, in Patent Document 1, no mention is made of silicone microparticles that comprise a core of a silicone rubber spherical microparticle formed from an addition reaction cured product of a monovalent olefinic unsaturated group-containing organopolysiloxane containing a small amount of monovalent olefinic unsaturated groups and an organohydrogenpolysiloxane containing a small amount of hydrogen atoms bonded to silicon atoms and that are capable of absorbing a large amount of low-viscosity silicones.

[Patent Document 1] U.S. Pat. No. 5,538,793

SUMMARY OF THE INVENTION

An object of the present invention is to provide silicone microparticles that are capable of absorbing a large amount of a low-viscosity polymethylsiloxane having a viscosity of not more than 10 mm$^2$/s, which represents a low-viscosity silicone, and are also able to suppress the greasiness, stickiness, and oily film feeling of cosmetic materials containing this type of polymethylsiloxane. Another object of the present invention is to provide a method of producing such silicone microparticles.

As a result of intensive research, the inventors of the present invention discovered that the above objects could be achieved by using the silicone microparticles described below, and inventors were therefore able to complete the present invention.

In other words, a first aspect of the present invention provides:

silicone microparticles comprising 100 parts by mass of silicone elastomer spherical microparticles having a volume average particle diameter within a range from 0.1 to 100 μm, and 0.5 to 25 parts by mass of a polyorganosilsesquioxane that coats the surface of the silicone elastomer spherical microparticles, wherein the silicone elastomer is capable of absorbing not less than 200 parts by mass of a polymethylsiloxane having a viscosity at 25° C. of not more than 10 mm$^2$/s per 100 parts by mass of the silicone elastomer.

A second aspect of the present invention provides a method of producing the silicone microparticles described above, the method comprising:

hydrolyzing and condensing an organotrialkoxysilane in a water medium, in the presence of silicone elastomer spherical microparticles having a volume average particle diameter within a range from 0.1 to 100 μm and an alkaline material, thereby coating the surface of the silicone elastomer spherical microparticles with a polyorganosilsesquioxane, wherein the silicone elastomer is capable of absorbing not less than 200 parts by mass of a polymethylsiloxane having a viscosity at 25° C. of not more than 10 mm$^2$/s per 100 parts by mass of the silicone elastomer.

A third aspect of the present invention provides a method of absorbing a polymethylsiloxane having a viscosity at 25° C. of not more than 10 mm$^2$/s, the method comprising:

bringing the polymethylsiloxane into contact with the silicone microparticles described above, and absorbing the polymethylsiloxane into the silicone microparticles.

A fourth aspect of the present invention provides use of the above silicone microparticles as an absorbent for a polymethylsiloxane having a viscosity at 25° C. of not more than 10 mm$^2$/s.

The silicone microparticles of the present invention are capable of absorbing a large amount of a low-viscosity polymethylsiloxane having a viscosity at of not more than 10 mm$^2$/s, which represents a low-viscosity silicone. Accordingly, it is expected that these silicone microparticles will have an effect of suppressing the greasiness, stickiness, and oily film feeling of cosmetic materials containing this type of polymethylsiloxane.

DETAILED DESCRIPTION OF THE PREFERRED EMBODIMENTS

A more detailed description of the present invention is provided below. In the following description, viscosity values refer to kinetic viscosity values measured at 25° C. using an Ostwald viscometer.

[Silicone Elastomer Spherical Microparticles]

In the silicone microparticles of the present invention, the silicone elastomer spherical microparticles that are surface-coated with a polyorganosilsesquioxane have a volume average particle diameter that is within a range from 0.1 to 100 μm, and preferably from 1 to 40 μm. If this volume average particle diameter is less than 0.1 μm, then the resulting silicone microparticles are less likely to exhibit the desired silkiness and smoothness. If the volume average particle diameter exceeds 100 μm, then the degree of silkiness and smoothness of the resulting silicone microparticles tends to deteriorate, and a feeling of grittiness may also develop. The volume average particle diameter is measured using a Coulter counter method. Further, in this description, the term "spherical" includes not only microparticles having a perfectly spherical shape, but also microparticles having deformed spherical shapes in which the average of the ratio (length of longest axis)/(length of shortest axis) (namely, the aspect ratio) is typically within a range from 1 to 4, preferably from 1 to 2, more preferably from 1 to 1.6, and still more preferably from 1 to 1.4. The shapes of the microparticles can be confirmed by inspecting the microparticles under an optical microscope.

The silicone elastomer that constitutes the silicone elastomer spherical microparticles preferably exhibits no stickiness, and preferably has a rubber hardness, measured using a type A durometer prescribed in HS K 6253, that is within a range from 5 to 90, and more preferably from 10 to 80. Provided the rubber hardness is within a range from 5 to 90, cohesion of the obtained silicone microparticles can be adequately suppressed, and microparticles having excellent levels of flowability and dispersibility, and superior feelings of silkiness, smoothness and softness can be obtained.

The silicone elastomer is capable of absorbing not less than 200 parts by mass of a polymethylsiloxane having a viscosity at 25° C. of not more than 10 mm²/s per 100 parts by mass of the silicone elastomer. If the amount of the polymethylsiloxane absorbed is less than 200 parts by mass, then the effect of the obtained silicone microparticles in suppressing the greasiness, stickiness, and oily film feeling of cosmetic materials containing such polymethylsiloxanes tends to weaken. The greater the amount of polymethylsiloxane absorbed the better, and therefore there are no particular limitations on the upper limit for the absorption amount, although for practical reasons, the absorption amount may be, for example, not more than 1,000 parts by mass, and particularly not more than 500 parts by mass.

The structure of the polymethylsiloxane may be a linear, cyclic or branched structure. Examples of the polymethylsiloxane include dimethylpolysiloxanes represented by the formula: $(CH_3)_3SiO[(CH_3)_2SiO]_nSi(CH_3)_3$ (wherein n is a positive number that satisfies $1 \leq n \leq 15$), decamethylcyclopentasiloxane, and the methylsiloxane represented by the formula: $[(CH_3)_3SiO]_3SiCH_3$.

The silicone elastomer is preferably a cured product of a liquid silicone composition comprising:

(A)

(A1) an organopolysiloxane represented by an average composition formula (1) shown below:

$$R^1_a R^2_b SiO_{(4-a-b)/2} \quad (1)$$

(wherein $R^1$ represents an unsubstituted or substituted monovalent hydrocarbon group of 1 to 30 carbon atoms excluding aliphatic unsaturated groups, $R^2$ represents a monovalent olefinic unsaturated group of 2 to 6 carbon atoms, and a and b are positive numbers that satisfy $0<a<3$, $0<b\leq3$, and $0.1 \leq a+b \leq 3$, provided that the proportion of monovalent hydrocarbon groups of 6 to 30 carbon atoms is less than 5 mol % of all the $R^1$ groups),
in which not less than 90 mol % of all the siloxane units other than the siloxane units at the molecular terminals are dimethylsiloxane units represented by a formula: $-(CH_3)_2SiO-$, and having a molecular weight of not less than 5,000, having two monovalent olefinic unsaturated groups within each molecule, and having a monovalent olefinic unsaturated group content of not more than 0.04 mol/100 g, (A2) an organopolysiloxane represented by the above average composition formula (1), in which not less than 90 mol % of all the siloxane units other than the siloxane units at the molecular terminals are dimethylsiloxane units represented by a formula: $-(CH_3)_2SiO-$, and having a molecular weight of not less than 5,000, having at least three monovalent olefinic unsaturated groups within each molecule, and having a monovalent olefinic unsaturated group content of not more than 0.06 mol/100 g, or a combination of component (A1) and component (A2), (B)

(B1) an organohydrogenpolysiloxane represented by an average composition formula (2) shown below:

$$R^3_c H_d SiO_{(4-c-d)/2} \quad (2)$$

(wherein $R^3$ represents an unsubstituted or substituted monovalent hydrocarbon group of 1 to 30 carbon atoms excluding aliphatic unsaturated groups, and c and d are positive numbers that satisfy $0<c<3$, $0<d\leq3$, and $0.1 \leq c+d \leq 3$, provided that the proportion of monovalent hydrocarbon groups of 6 to 30 carbon atoms is less than 5 mol % of all the $R^3$ groups),
in which not less than 90 mol % of all the siloxane units other than the siloxane units at the molecular terminals are dimethylsiloxane units represented by a formula: $-(CH_3)_2SiO-$, and having a molecular weight of not less than 5,000, having two hydrogen atoms bonded to silicon atoms within each molecule, and having a silicon atom-bonded hydrogen atom content of not more than 0.04 mol/100 g, (B2) an organohydrogenpolysiloxane represented by the above average composition formula (2), in which not less than 90 mol % of all the siloxane units other than the siloxane units at the molecular terminals are dimethylsiloxane units represented by a formula: $-(CH_3)_2SiO-$, and having a molecular weight of not less than 5,000, having at least three hydrogen atoms bonded to silicon atoms within each molecule, and having a silicon atom-bonded hydrogen atom content of not more than 0.06 mol/100 g, or a combination of component (B1) and component (B2), in an amount that yields from 0.5 to 2 hydrogen atoms bonded to silicon atoms within component (B) per monovalent olefinic unsaturated group within component (A), and (C) a platinum group metal-based catalyst, provided that when component (A) is component (A1), component (B) is either component (B2) or a combination of component (B1) and component (B2).

Component (A)

The component (A) is an organopolysiloxane having monovalent olefinic unsaturated groups within each molecule, and may be either the component (A1), the component (A2), or a combination of the component (A1) and the component (A2). The component (A1) and the component (A2) may each employ either a single compound or a combination of two or more compounds.

Preferably, a and b are positive numbers that satisfy $0<a\leq2.295$, $0.005\leq b\leq2.3$, and $0.5\leq a+b\leq2.3$.

The number of carbon atoms within $R^1$ is typically within a range from 1 to 30, and is preferably from 1 to 20, and more preferably from 1 to 6. Specific examples of $R^1$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group, icosyl group, henicosyl group, docosyl group, tricosyl group, tetracosyl group or triacontyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom) and a substituent such as an acryloyloxy group, methacryloyloxy group, epoxy group, glycidoxy group or carboxyl group.

The proportion of monovalent hydrocarbon groups of 6 to 30 carbon atoms within all of the $R^1$ groups is typically less than 5 mol % (namely, at least 0 mol % and less than 5 mol %), and is preferably not more than 2 mol % (namely, from 0 to 2 mol %). If this proportion is 5 mol % or greater, then the amount of the aforementioned polymethylsiloxane absorbed by the obtained silicone microparticles tends to decrease.

The number of carbon atoms with $R^2$ is typically from 2 to 6. Specific examples of $R^2$ include a vinyl group, allyl group, propenyl group, butenyl group, pentenyl group or hexenyl group. From an industrial perspective, a vinyl group is preferred.

In the organopolysiloxane of the component (A), the amount of dimethylsiloxane units represented by the formula —$(CH_3)_2SiO$— represents not less than 90 mol % (namely, 90 to 100 mol %), and preferably not less than 95 mol % (namely, 95 to 100 mol %) of all the siloxane units other than the siloxane units at the molecular terminals (hereafter, also referred to as "all the non-terminal siloxane units"). If this amount is less than 90 mol %, then the amount of the aforementioned polymethylsiloxane absorbed by the obtained silicone microparticles tends to decrease.

In the organopolysiloxane of the component (A), of the siloxane units other than the siloxane units at the molecular terminals (hereafter, these siloxane units may also be referred to as "the non-terminal siloxane units"), examples of the siloxane units other than the dimethylsiloxane units represented by the formula —$(CH_3)_2SiO$— include $R^{11}{}_2SiO_{2/2}$ units, $R^1R^2SiO_{2/2}$ units, $R^2{}_2SiO_{2/2}$ units, $R^1SiO_{3/2}$ units, $R^2SiO_{3/2}$ units and $SiO_{4/2}$ units (wherein $R^{11}$ represents an unsubstituted or substituted monovalent hydrocarbon group of 2 to 30 carbon atoms, preferably 2 to 20 carbon atoms, and more preferably 2 to 6 carbon atoms, excluding aliphatic unsaturated groups, and $R^1$ and $R^2$ are as defined above).

Specific examples of $R^{11}$ include the same monovalent hydrocarbon groups as those exemplified above for $R^{11}$ excluding the unsubstituted methyl group and substituted methyl groups.

In the organopolysiloxane of the component (A), the amount of the non-terminal siloxane units that are other than dimethylsiloxane units represented by the formula —$(CH_3)_2SiO$— is typically not more than 10 mol % (namely, 0 to 10 mol %), and preferably not more than 5 mol % (namely, 0 to 5 mol %) of all the non-terminal siloxane units. If this amount exceeds 10 mol %, then the amount of the aforementioned polymethylsiloxane absorbed by the obtained silicone microparticles tends to decrease. In those cases where the amount of at least one type of unit amongst $R^1SiO_{3/2}$ units, $R^2SiO_{3/2}$ units (wherein $R^1$ and $R^2$ are as defined above) and $SiO_{4/2}$ units is large, the resulting silicone microparticles tend to be particularly prone to a reduction in the amount of polymethylsiloxane absorbed, and therefore the combined amount of these siloxane units is preferably not more than 2 mol % (namely, 0 to 2 mol %) of all the non-terminal siloxane units.

In the organopolysiloxane of the component (A), examples of the siloxane units at the molecular terminals include $R^1{}_3SiO_{1/2}$ units, $R^1{}_2R^2SiO_{1/2}$ units, $R^1R^2{}_2SiO_{1/2}$ units, and $R^2{}_3SiO_{1/2}$ units (wherein $R^1$ and $R^2$ are as defined above).

The molecular weight of the organopolysiloxane of the component (A) is typically not less than 5,000, and is preferably 8,000 or greater. If this molecular weight is less than 5,000, then the amount of the aforementioned polymethylsiloxane absorbed by the obtained silicone microparticles tends to decrease. On the other hand, the molecular weight is preferably not more than 200,000. Provided the molecular weight is not more than 200,000, the viscosity of the component (A) can be prevented from becoming overly high, and the production method described below can be used to easily generate silicone microparticles having a narrow particle size distribution.

In the organopolysiloxane of the component (A1), the monovalent olefinic unsaturated group content is typically not more than 0.04 mol/100 g, and is preferably not more than 0.02 mol/100 g. Further, in the organopolysiloxane of the component (A2), the monovalent olefinic unsaturated group content is typically not more than 0.06 mol/100 g, and is preferably not more than 0.04 mol/100 g. In those cases where the monovalent olefinic unsaturated group content within the component (A1) exceeds 0.04 mol/100 g, or the monovalent olefinic unsaturated group content within the component (A2) exceeds 0.06 mol/100 g, or both these conditions apply, the amount of the aforementioned polymethylsiloxane absorbed by the obtained silicone microparticles tends to decrease. Although there are no particular restrictions on the lower limit for the monovalent olefinic unsaturated group content, for practical reasons, the monovalent olefinic unsaturated group content in the component (A1) may be, for example, 0.001 mol/100 g or greater, and the monovalent olefinic unsaturated group content in the component (A2) may be, for example, 0.0015 mol/100 g or greater.

Component (B)

The component (B) is an organohydrogenpolysiloxane comprising hydrogen atoms bonded to silicon atoms (hereafter also referred to as "SiH groups") within each molecule. The component (B) may be either the component (B1), the component (B2), or a combination of the component (B1) and the component (B2). The component (B1) and the component (B2) may each employ either a single compound or a combination of two or more compounds.

Preferably, c and d are positive numbers that satisfy $0 < c \leq 2.295$, $0.005 \leq d \leq 2.3$, and $0.5 \leq c+d \leq 2.3$.

The number of carbon atoms within $R^3$ is typically within a range from 1 to 30, and is preferably from 1 to 20, and more preferably from 1 to 6. Specific examples of $R^3$ include the same groups as those exemplified above for $R^1$.

The proportion of monovalent hydrocarbon groups of 6 to 30 carbon atoms within all of the $R^3$ groups is typically less than 5 mol % (namely, at least 0 mol % and less than 5 mol %), and is preferably not more than 2 mol % (namely, from 0 to 2 mol %). If this proportion is 5 mol % or greater, then the amount of the aforementioned polymethylsiloxane absorbed by the obtained silicone microparticles tends to decrease.

In the organohydrogenpolysiloxane of the component (B), the amount of dimethylsiloxane units represented by the formula —$(CH_3)_2SiO$— represents not less than 90 mol % (namely, 90 to 100 mol %), and preferably not less than 95 mol % (namely, 95 to 100 mol %) of all the siloxane units other than the siloxane units at the molecular terminals. If this amount is less than 90 mol %, then the amount of the aforementioned polymethylsiloxane absorbed by the obtained silicone microparticles tends to decrease.

In the organohydrogenpolysiloxane of the component (B), examples of the non-terminal siloxane units other than the dimethylsiloxane units represented by the formula —$(CH_3)_2SiO$— include $R^{31}{}_2SiO_{2/2}$ units, $R^3HSiO_{2/2}$ units, $H_2SiO_{2/2}$ units, $R^3SiO_{3/2}$ units, $HSiO_{3/2}$ units and $SiO_{4/2}$ units (wherein $R^{31}$ represents an unsubstituted or substituted monovalent hydrocarbon group of 2 to 30 carbon atoms, preferably 2 to 20 carbon atoms, and more preferably 2 to 6 carbon atoms, excluding aliphatic unsaturated groups, and $R^3$ is as defined above).

Specific examples of $R^{31}$ include the same monovalent hydrocarbon groups as those exemplified above for $R^1$ excluding the unsubstituted methyl group and substituted methyl groups.

In the organohydrogenpolysiloxane of the component (B), the amount of the non-terminal siloxane units that are other than dimethylsiloxane units represented by the formula —$(CH_3)_2SiO$— is typically not more than 10 mol % (namely, 0 to 10 mol %), and preferably not more than 5 mol % (namely, 0 to 5 mol %) of all the non-terminal siloxane units. If this amount exceeds 10 mol %, then the amount of the aforementioned polymethylsiloxane absorbed by the obtained silicone microparticles tends to decrease. In those cases where the amount of at least one type of unit amongst $R^3SiO_{3/2}$ units, $HSiO_{3/2}$ units (wherein $R^3$ is as defined above) and $SiO_{4/2}$ units is large, the resulting silicone microparticles tend to be particularly prone to a reduction in the amount of polymethylsiloxane absorbed, and therefore the combined amount of these siloxane units is preferably not more than 2 mol % (namely, 0 to 2 mol %) of all the non-terminal siloxane units.

In the organohydrogenpolysiloxane of the component (B), examples of the siloxane units at the molecular terminals include $R^3{}_3SiO_{1/2}$ units, $R^3{}_2HSiO_{1/2}$ units, $R^3H_2SiO_{1/2}$ units, and $H_3SiO_{1/2}$ units (wherein $R^3$ is as defined above).

The molecular weight of the organohydrogenpolysiloxane of the component (B) is typically not less than 5,000, and is preferably 8,000 or greater. If this molecular weight is less than 5,000, then the amount of the aforementioned polymethylsiloxane absorbed by the obtained silicone microparticles tends to decrease. On the other hand, the molecular weight is preferably not more than 200,000. Provided the molecular weight is not more than 200,000, the viscosity of the component (B) can be prevented from becoming overly high, and the production method described below can be used to easily generate silicone microparticles having a narrow particle size distribution.

In the organohydrogenpolysiloxane of the component (B1), the SiH group content is typically not more than 0.04 mol/100 g, and is preferably not more than 0.02 mol/100 g. Further, in the organohydrogenpolysiloxane of the component (B2), the SiH group content is typically not more than 0.06 mol/100 g, and is preferably not more than 0.04 mol/100 g. In those cases where the SiH group content within the component (B1) exceeds 0.04 mol/100 g, or the SiH group content within the component (B2) exceeds 0.06 mol/100 g, or both these conditions apply, the amount of the aforementioned polymethylsiloxane absorbed by the obtained silicone microparticles tends to decrease. Although there are no particular restrictions on the lower limit for the SiH group content, for practical reasons, the SiH group content in the component (B1) may be, for example, 0.001 mol/100 g or greater, and the SiH group content in the component (B2) may be, for example, 0.0015 mol/100 g or greater.

When the component (A) is component (A1), the component (B) is either component (B2) or a combination of component (B1) and component (B2). In other words, the combination where the component (A) is component (A1) and the component (B) is component (B1) is excluded from the combinations of component (A) and component (B) used for obtaining the silicone elastomer described above. This is because the elastomer cured product obtained from this combination tends to be prone to developing stickiness.

As mentioned above, the blend amount of the component (B) yields from 0.5 to 2 SiH groups within the component (B) per monovalent olefinic unsaturated group within the component (A), and this number of SiH groups is preferably within a range from 0.7 to 1.5. If an amount of the component (B) that yields fewer than 0.5 or more than 2 SiH groups is added to the liquid silicone composition, then the resulting elastomer cured product tends to develop stickiness, and also tends to exhibit reaction activity that is overly high.

Component (C)

The platinum group metal-based catalyst of the component (C) is a catalyst that promotes the addition reaction between the monovalent olefinic unsaturated groups within the component (A) and the SiH groups within the component (B). The component (C) may use either a single catalyst or a combination of two or more different catalysts.

Any of the conventional catalysts used in hydrosilylation reactions may be used as the component (C), and specific examples include platinum group metals such as platinum (including platinum black), rhodium and palladium; platinum chlorides, chloroplatinic acids and chloroplatinates such as $H_2PtCl_4 \cdot kH_2O$, $H_2PtCl_6 \cdot kH_2O$, $NaHPtCl_6 \cdot kH_2O$, $KHPtCl_6 \cdot kH_2O$, $Na_2PtCl_6 \cdot kH_2O$, $K_2PtCl_4 \cdot kH_2O$, $PtCl_4 \cdot kH_2O$, $PtCl_2$ and $Na_2HPtCl_4 \cdot kH_2O$ (wherein, k represents an integer of 0 to 6, and is preferably either 0 or 6); alcohol-modified chloroplatinic acid (see U.S. Pat. No. 3,220,972); complexes of chloroplatinic acid and olefins (see U.S. Pat. Nos. 3,159,601, 3,159,662 and 3,775,452); a platinum group metal such as platinum black or palladium supported on a carrier such as alumina, silica or carbon; rhodium-olefin complexes; chlorotris(triphenylphosphine)rhodium (Wilkinson's catalyst); and complexes of a platinum chloride, a chloroplatinic acid or a chloroplatinate with a vinyl group-containing siloxane and particularly a vinyl group-containing cyclic siloxane.

The blend amount of the component (C) need only be sufficient to function as an effective hydrosilylation reaction catalyst, and the mass of the platinum group metal within the component (C) relative to the total mass of the composition, is typically within a range from 0.1 to 500 ppm, and is preferably from 0.5 to 200 ppm, and more preferably from 1 to 100 ppm.

Method of Producing Silicone Elastomer Spherical Microparticles

The silicone elastomer spherical microparticles can be produced in the form of a water dispersion using conventional methods. One possible method involves adding a surfactant and water to a mixed solution of an olefinic unsaturated group-containing organopolysiloxane and an organohydrogenpolysiloxane, performing an emulsification to generate an emulsion, and then adding a platinum group metal-based catalyst to initiate an addition reaction.

In this method, an example of the olefinic unsaturated group-containing organopolysiloxane is the component (A) described above, an example of the organohydrogenpolysiloxane is the component (B), and an example of the platinum group metal-based catalyst is the component (C).

Further, there are no particular restrictions on the surfactant, and examples include nonionic surfactants such as polyoxyethylene alkyl ethers, polyoxyethylene polyoxypropylene alkyl ethers, polyoxyethylene alkylphenyl ethers, polyethylene glycol aliphatic acid esters, sorbitan aliphatic acid esters, polyoxyethylene sorbitan aliphatic acid esters, polyoxyethylene sorbitol aliphatic acid esters, glycerol aliphatic acid esters, polyoxyethylene glycerol aliphatic acid esters, polyglycerol aliphatic acid esters, propylene glycol aliphatic acid esters, polyoxyethylene castor oils, polyoxyethylene hardened castor oils, polyoxyethylene hardened castor oil aliphatic acid esters, polyoxyethylene alkylamines, polyoxyethylene aliphatic acid amides, polyoxyethylene-modified organopolysiloxanes, and polyoxyethylene polyoxypropylene-modified organopolysiloxanes; anionic surfactants such as alkyl sulfates, polyoxyethylene alkyl ether sulfates, polyoxyethylene alkylphenyl ether sulfates, N-acyltaurinates, alkylbenzene sulfonates, polyoxyethylene alkylphenyl ether sulfonates, α-olefin sulfonates, alkylnaphthalene sulfonates, alkyl diphenyl ether disulfonates, dialkyl sulfosuccinates, monoalkyl sulfosuccinates, polyoxyethylene alkyl ether sulfosuccinates, aliphatic acid salts, polyoxyethylene alkyl ether acetates, N-acylamino acid salts, alkenylsuccinates, alkyl phosphates, polyoxyethylene alkyl ether phosphates, polystyrene sulfonates, formalin condensates of naphthalene sulfonic acid, formalin condensates of aromatic sulfonic acids, carboxylic acid polymers, and styrene oxyalkylene acid anhydride copolymers; cationic surfactants such as alkyltrimethylammonium salts, dialkyldimethylammonium salts, polyoxyethylene alkyldimethylammonium salts, dipolyoxyethylene alkylmethylammonium salts, tripolyoxyethylene alkylammonium salts, alkylbenzyldimethylammonium salts, alkylpyridinium salts, monoalkylamine salts, monoalkylamide amine salts, and cationized cellulose; and amphoteric surfactants such as alkyl dimethylamine oxides, alkyl dimethylcarboxybetaines, alkylamide propyl dimethylcarboxybetaines, alkyl hydroxysulfobetaines, and alkylcarboxymethyl hydroxyethyl imidazolinium betaines. These surfactants may be used individually, or two or more different surfactants may be used in combination. An anionic surfactant and a cationic surfactant may not be used in combination.

The emulsification can be performed using a typical emulsification disperser, examples of which include high-speed rotational centrifugal radial stirrers such as a homodisper, high-speed rotational shearing stirrers such as a homomixer, high-pressure injection-type emulsification dispersers such as a homogenizer, colloid mills, and ultrasonic emulsifiers.

In those cases where the platinum group metal-based catalyst exhibits poor dispersibility within water, the catalyst is preferably dissolved in a surfactant prior to addition to the emulsion. Examples of this surfactant include the same surfactants as those exemplified above.

The addition reaction may be conducted at room temperature, although in those cases where the reaction does not proceed to completion at room temperature, the reaction may be conducted under heating at a temperature of less than 100° C.

[Polyorganosilsesquioxane]

The silicone microparticles of the present invention are composed of silicone elastomer spherical microparticles coated with a polyorganosilsesquioxane, and the amount of the polyorganosilsesquioxane is typically within a range from 0.5 to 25 parts by mass, and preferably from 1 to 15 parts by mass, per 100 parts by mass of the silicone elastomer spherical microparticles described above. If the amount of the polyorganosilsesquioxane is less than 0.5 parts by mass, then the resulting silicone microparticles tend to exhibit powerful cohesiveness, and the flowability, dispersibility, silkiness and smoothness of the microparticles tend to deteriorate. In contrast, if the amount of the polyorganosilsesquioxane exceeds 25 parts by mass, then the resulting silicone microparticles tend to lose their feeling of softness, and the amount of the aforementioned polymethylsiloxane absorbed tends to decrease.

In the silicone microparticles of the present invention, the surface of the silicone elastomer spherical microparticles is not coated with the polyorganosilsesquioxane in such a manner that leaves absolutely no gaps in the coating. If the coating is formed with absolutely no gaps, then the silicone elastomer spherical microparticles are no longer able to absorb the polymethylsiloxane. By using the production method outlined below, surface-coated silicone microparticles can be obtained in which the surface coating includes gaps that are sufficient to allow passage of the polymethylsiloxane.

Examples of the polyorganosilsesquioxane include polymers comprising units represented by the formula $R^4SiO_{3/2}$ (wherein $R^4$ represents an unsubstituted or substituted monovalent hydrocarbon group of 1 to 20 carbon atoms, and preferably 1 to 6 carbon atoms). Specific examples of $R^4$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group or icosyl group; alkenyl groups such as a vinyl group or allyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom) and a substituent such as an amino group, acryloyloxy group, methacryloyloxy group, epoxy group, glycidoxy group, mercapto group or carboxyl group.

In order to obtain the silicone microparticles of the present invention using the production method described below, preferably not less than 50 mol % (namely, 50 to 100 mol %), more preferably not less than 70 mol % (namely, 70 to 100 mol %), and particularly preferably 80 mol % or more (namely, 80 to 100 mol %) of all the $R^4$ groups within the polyorganosilsesquioxane are methyl groups.

The polyorganosilsesquioxane may also include, besides the $R^4SiO_{3/2}$ units, at least one type of unit selected from among $R^4{}_2SiO_{2/2}$ units, $R^4{}_3SiO_{1/2}$ units and $SiO_{4/2}$ units (wherein $R^4$ is as defined above), provided the inclusion of this other type of unit does not impair the favorable feelings during use of the obtained silicone microparticles, such as feelings of silkiness or smoothness, nor impair the other properties of the silicone microparticles such as the soft feeling, the lack of cohesiveness, and the dispersibility. In this type of polyorganosilsesquioxane, the proportion of $R^4SiO_{3/2}$ units within the total number of all siloxane units is preferably within a range from 70 to 100 mol %, and is more preferably from 80 to 100 mol %.

[Production Method]

The coating of the surface of a particle with another material belongs to the field of particle complexing techniques, and numerous methods have been proposed for achieving this type of coating. Examples of such methods include methods in which particles that act as the core (hereafter referred to as "core particles") and particles that are used for coating the surface of the core particles (hereafter referred to as "coating material particles") are subjected to dry mixing, thereby adhering the coating material particles to the surface of the core particles, and methods in which the dry mixed particles are subsequently subjected to processing that imparts an impact force, a compressive force, a frictional force or a shearing force or the like to the particles, thereby fixing the coating material particles to the surface of the core particles in the form of a film. However, because silicone elastomer particles exhibit powerful cohesion, adhering a uniform thin film of coating material particles to the surface of the silicone elastomer particles by dry mixing is problematic. Further, because the silicone elastomer particles also exhibit elasticity, the coating material particles cannot be satisfactorily fixed to the surface of the silicone elastomer particles even if an impact force, a compressive force, a frictional force or a shearing force or the like is applied to the particles. Another method exists that involves producing the coated particles by spray drying a dispersion of the core particles and the coating material particles, but this method tends to also produce aggregated particles, particles composed solely of the coating material particles, or both these types of particles.

Accordingly, the silicone microparticles of the present invention are preferably produced using the method disclosed in Patent Document 1. In other words, the silicone microparticles are preferably produced by hydrolyzing and condensing an organotrialkoxysilane in a water medium, in the presence of the aforementioned silicone elastomer spherical microparticles having a volume average particle diameter within a range from 0.1 to 100 μm and an alkaline material, thereby coating the surface of the silicone elastomer spherical microparticles with a polyorganosilsesquioxane. The water medium, the silicone elastomer spherical microparticles, the alkaline material and the organotrialkoxysilane may be either added simultaneously or added at different times, although from the viewpoint of reactivity, the organotrialkoxysilane is preferably added to a water dispersion of the silicone elastomer spherical microparticles that already contains the added alkaline material.

The alkaline material functions as a catalyst for the hydrolysis-condensation reaction of the organotrialkoxysilane. The alkaline material may be either a single material or a combination of two or more different materials. The alkaline material may be either added as is, or added in the form of an alkaline aqueous solution. The amount added of the alkaline material is adjusted so that the pH of the water dispersion of the silicone elastomer spherical microparticles containing the alkaline material is preferably within a range from 10.0 to 13.0, and more preferably from 10.5 to 12.5. Provided the amount of the alkaline material yields a pH within a range from 10.0 to 13.0, the hydrolysis-condensation reaction of the organotrialkoxysilane, and the coating of the surface of the silicone elastomer spherical microparticles by the polyorganosilsesquioxane both proceed favorably.

There are no particular restrictions on the alkaline material, and specific examples of materials that may be used include alkali metal hydroxides such as potassium hydroxide, sodium hydroxide and lithium hydroxide; alkaline earth metal hydroxides such as calcium hydroxide and barium hydroxide; alkali metal carbonates such as potassium carbonate and sodium carbonate; ammonia; tetraalkylammonium hydroxides such as tetramethylammonium hydroxide and tetraethylammonium hydroxide; and amines such as monomethylamine, monoethylamine, monopropylamine, monobutylamine, monopentylamine, dimethylamine, diethylamine, trimethylamine, triethanolamine and ethylenediamine. Of these, ammonia is the most desirable as it can be readily removed from the powder of the resulting silicone microparticles by volatilization. Commercially available aqueous solutions of ammonia may be used as the ammonia.

Examples of the organotrialkoxysilane include compounds represented by a formula: $R^4Si(OR^5)_3$ (wherein $R^4$ is as defined above, and $R^5$ represents an unsubstituted monovalent hydrocarbon group of 1 to 6 carbon atoms). Specific examples of $R^5$ include a methyl group, ethyl group, propyl group, butyl group, pentyl group or hexyl group, although in terms of reactivity, a methyl group is preferred. In those cases where it is desirable to introduce at least one type of other unit selected from among $R^4_2SiO_{2/2}$ units, $R^4_3SiO_{1/2}$ units and $SiO_{4/2}$ units into the polyorganosilsesquioxane, at least one of the corresponding compounds, namely at least one of $R^4_2Si(OR^5)_2$, $R^4_3SiOR^5$ and $Si(OR^5)_4$, respectively, may also be added. (In the above formulas, $R^4$ and $R^5$ are as defined above). In those cases where $R^4Si(OR^5)_3$, and at least one of $R^4_2Si(OR^5)_2$, $R^4_3SiOR^5$ and $Si(OR^5)_4$ (wherein $R^4$ and $R^5$ are as defined above) are used as the raw materials for the polyorganosilsesquioxane, the proportion of the $R^4Si(OR^5)_3$ within the combined total of all the raw materials is preferably within a range from 70 to 100 mol %, and is more preferably from 80 to 100 mol %.

The amount added of the organotrialkoxysilane is adjusted so that the amount of the polyorganosilsesquioxane is typically within a range from 0.5 to 25 parts by mass, and preferably from 1 to 15 parts by mass, per 100 parts by mass of the silicone elastomer spherical microparticles.

The addition of the organotrialkoxysilane is preferably performed under stirring with a typical stirring device such as a propeller blade or a flat blade or the like. The organotrialkoxysilane may be added in a single batch, but is preferably added gradually over a period of time. Further, the temperature during the addition is preferably within a range from 0 to 60° C., and is more preferably from 0 to 40° C. Provided this temperature is within a range from 0 to 60° C., the surface of the silicone elastomer spherical microparticles can be coated with the polyorganosilsesquioxane in a more favorable state.

The stirring is continued following the addition of the organotrialkoxysilane, until the hydrolysis-condensation reaction of the organotrialkoxysilane is complete. In order to complete the hydrolysis-condensation reaction, the reaction may be conducted either at room temperature or under heating at a temperature within a range from 40 to 100° C.

Following the hydrolysis-condensation reaction, water is removed from the water dispersion of the obtained silicone microparticles of the present invention. This removal of the water is performed, for example, by heating the water dispersion at normal pressure or under reduced pressure following completion of the reaction, and more specific examples include a method in which the water is removed by leaving the dispersion to stand under heat, a method in which the water is removed while the dispersion is stirred and flowed under heat, a method in which the dispersion is sprayed and dispersed in a hot air stream such as by use of a spray drier, and methods that employ a fluid heating medium. Prior to this water removal operation, a pretreatment may be used to concentrate the dispersion using a method such as thermal dehydration, separation by filtration, centrifugal separation, or decantation. Moreover, if necessary, the dispersion may be washed with water.

In those cases where the product obtained upon removal of the water from the dispersion following reaction is an aggregate, the silicone microparticles can be obtained by crushing the product using a crushing device such as a jet mill, ball mill or hammer mill.

EXAMPLES

A more detailed description of the present invention is presented below based on a series of examples and comparative examples, although the present invention is in no way limited by these examples. In the examples, unless stated otherwise, "%" values representing concentration or content refer to "% by mass". Furthermore, a "dimethylsiloxane unit content" refers to the proportion (mol %) of dimethylsiloxane units represented by the formula: —(CH$_3$)$_2$SiO— relative to all the non-terminal siloxane units within the polysiloxane that corresponds with the component (A) or the component (B).

Example 1

A glass beaker with a capacity of 1 liter was charged with 350 g of a methylvinylpolysiloxane A1 represented by formula (3) shown below and having a dimethylsiloxane unit content of 100 mol %, a molecular weight of 13,524 and a vinyl group content of 0.015 mol/100 g, and 160 g of a methylhydrogenpolysiloxane B1 represented by formula (4) shown below and having a dimethylsiloxane unit content of 98.7 mol %, a molecular weight of 11,369 and a SiH group content of 0.035 mol/100 g (an amount equivalent to 1.07 SiH groups within the methylhydrogenpolysiloxane B1 per vinyl group within the methylvinylpolysiloxane A1), and stirring and mixing were performed at 2,000 rpm using a homomixer. To the resulting mixed liquid were added 1.2 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 385 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 0.8 g of a toluene solution of a chloroplatinic acid-olefin complex (platinum content: 0.5%), 1.5 g of a polyoxyethylene lauryl ether (number of mols of added ethylene oxide=4 mol), and 1.5 g of a polyoxyethylene lauryl ether (number of mols of added ethylene oxide=23 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a particle size distribution measuring apparatus "Multisizer 3" (a product name, manufactured by Beckman Coulter, Inc.) yielded a result of 12 μm.

882 g of the thus obtained water dispersion of silicone elastomer spherical microparticles was transferred to a glass flask with a capacity of 3 liters fitted with a stirring device having an anchor-shaped stirring blade, and 2,003 g of water and 57 g of 28% ammonia water were added to the flask. The pH of the liquid at this point was 11.2. Following lowering of the temperature to 5 to 10° C., 58 g of methyltrimethoxysilane (an amount that yields 6.3 parts by mass of a polymethylsilsesquioxane following the hydrolysis and condensation reaction per 100 parts by mass of the silicone elastomer spherical microparticles) was added dropwise to the flask over a period of 25 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the methyltrimethoxysilane.

The thus obtained methyltrimethoxysilane hydrolysis-condensation reaction liquid was dewatered to a water content of approximately 30% using a pressure filtration device. The dewatered product was transferred to a stainless steel tray and dried at a temperature of 105° C. in a hot air circulating drier. The resulting dried product was crushed in a jet mill, yielding microparticles with good flowability. Inspection of these microparticles using an electron microscope revealed spherical particles, the surfaces of which were coated with particulate matter with a particle diameter of approximately 100 nm, confirming that silicone elastomer microparticles comprising the silicone elastomer spherical microparticles coated with a polyorganosilsesquioxane had been obtained. The thus obtained silicone microparticles were dispersed in water using a surfactant, and subsequent measurement of the volume average particle diameter using a Multisizer 3 yielded a result of 12 μm.

The methylvinylpolysiloxane A1, the methylhydrogenpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured into an aluminum Petri dish in an amount sufficient to generate a thickness of 10 mm. The mixture was left to stand at 25° C. for 24 hours, and was then heated for 1 hour in a thermostatic chamber at 50° C., thus forming a non-sticky silicone elastomer. Measurement of the hardness of this silicone elastomer using a type A durometer prescribed in JIS K 6253 revealed a result of 22.

The methylvinylpolysiloxane A1, the methylhydrogenpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured onto a Teflon (a registered trademark) tray in an amount sufficient to generate a thickness of approximately 1 mm. The mixture was left to stand at 25° C. for 24 hours, and was then heated for 1 hour in a thermostatic chamber at 50° C., thus forming a silicone elastomer sheet. Test pieces were prepared by cutting the obtained sheet into square pieces with a length along one side of approximately 30 mm, and following measurement of the mass of these test pieces, each test piece was immersed for 24 hours in one of the polymethylsiloxanes shown in Table 1. This caused the test piece to absorb the polymethylsiloxane and swell. Each test piece was then removed from the polymethylsiloxane, and following removal of any polymethylsiloxane on the test piece surface by wiping with a tissue, the mass of the test piece was re-measured. Table 1 lists the amount of the polymethylsiloxane absorbed (the oil absorption amount) by the silicone elastomer sheet per 1 g of the silicone elastomer.

5.0 g of the silicone microparticles obtained in the manner described above and 50 g of a polymethylsiloxane shown in Table 1 were placed in a 100 ml glass bottle, and after shaking for 30 minutes, the bottle was left to stand for 3 days at room temperature. A solid-liquid separation was then performed using pressure filtration, and the mass of the resulting cake-like solid fraction was measured. Table 1 lists the oil absorption amount per 5 g of the silicone microparticles, which was calculated using the formula: [mass (g) of solid fraction following solid-liquid separation]−5.0 (g).

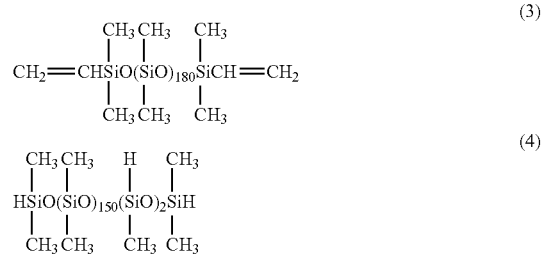

Example 2

A water dispersion of silicone elastomer microparticles was obtained in the same manner as example 1, with the exceptions of altering the amount of the methylvinylpolysiloxane A1 from 350 g to 270 g, and replacing the 160 g of the methylhydrogenpolysiloxane B1 with 240 g of a methylhydrogenpolysiloxane B2 represented by formula (5) shown below and having a dimethylsiloxane unit content of 99.3 mol %, a molecular weight of 22,484 and a SiH group content of 0.018 mol/100 g (an amount equivalent to 1.07 SiH groups within the methylhydrogenpolysiloxane B2 per vinyl group within the methylvinylpolysiloxane A1). Inspection of the shape of these silicone elastomer microparticles in the same manner as example 1 revealed spherical particles, and measurement of the volume average particle diameter in the same manner as example 1 yielded a result of 12 μm.

Using 882 g of the obtained water dispersion of silicone elastomer spherical microparticles as a raw material, a hydrolysis-condensation reaction and subsequent dewatering were conducted in the same manner as example 1, thus forming microparticles with good flowability. During this process, the pH of the liquid upon addition of the 2,003 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 12 μm.

With the exception of using the methylhydrogenpolysiloxane B2 instead of the methylhydrogenpolysiloxane B1, a non-sticky silicone elastomer was obtained in the same manner as example 1. Measurement of the hardness of this silicone elastomer using a type A durometer meter prescribed in JIS K 6253 yielded a result of 20.

With the exception of using the methylhydrogenpolysiloxane B2 instead of the methylhydrogenpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

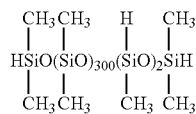
(5)

Example 3

A water dispersion of silicone elastomer microparticles was obtained in the same manner as example 1, with the exceptions of replacing the 350 g of the methylvinylpolysiloxane A1 with 170 g of a methylvinylpolysiloxane A2 represented by formula (6) shown below and having a dimethylsiloxane unit content of 98.9 mol %, a molecular weight of 13,696 and a vinyl group content of 0.029 mol/100 g, and replacing the 160 g of the methylhydrogenpolysiloxane B1 with 340 g of a methylhydrogenpolysiloxane B3 represented by formula (7) shown below and having a dimethylsiloxane unit content of 100 mol %, a molecular weight of 14,954 and a SiH group content of 0.013 mol/100 g (an amount equivalent to 0.90 SiH groups within the methylhydrogenpolysiloxane B3 per vinyl group within the methylvinylpolysiloxane A2). Inspection of the shape of these silicone elastomer microparticles in the same manner as example 1 revealed spherical particles, and measurement of the volume average particle diameter in the same manner as example 1 yielded a result of 11 μm.

Using 882 g of the obtained water dispersion of silicone elastomer spherical microparticles as a raw material, a hydrolysis-condensation reaction and subsequent dewatering were conducted in the same manner as example 1, thus forming microparticles with good flowability. During this process, the pH of the liquid upon addition of the 2,003 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 11 μm.

With the exceptions of using the methylvinylpolysiloxane A2 instead of the methylvinylpolysiloxane A1, and using the methylhydrogenpolysiloxane B3 instead of the methylhydrogenpolysiloxane B1, a non-sticky silicone elastomer was obtained in the same manner as example 1. Measurement of the hardness of this silicone elastomer using a type A durometer meter prescribed in JIS K 6253 yielded a result of 22.

With the exceptions of using the methylvinylpolysiloxane A2 instead of the methylvinylpolysiloxane A1, and using the methylhydrogenpolysiloxane B3 instead of the methylhydrogenpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

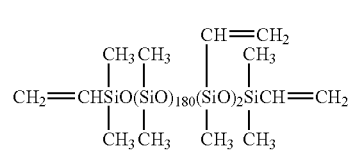
(6)

-continued

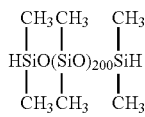
(7)

Comparative Example 1

A glass beaker with a capacity of 1 liter was charged with 500 g of the methylvinylpolysiloxane A1, and 19 g of a methylhydrogenpolysiloxane B4 represented by formula (8) shown below and having a dimethylsiloxane unit content of 75 mol %, a molecular weight of 2,393 and a SiH group content of 0.418 mol/100 g (an amount equivalent to 1.06 SiH groups within the methylhydrogenpolysiloxane B4 per vinyl group within the methylvinylpolysiloxane A1), and stirring and mixing were performed at 2,000 rpm using a homomixer. To the resulting mixed liquid were added 1.2 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 377 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 0.8 g of a toluene solution of a chloroplatinic acid-olefin complex (platinum content: 0.5%) and 1.8 g of a polyoxyethylene lauryl ether (number of mols of added ethylene oxide=9 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a Multisizer 3 yielded a result of 12 μm.

1,155 g of the thus obtained water dispersion of silicone elastomer spherical microparticles was transferred to a glass flask with a capacity of 3 liters fitted with a stirring device having an anchor-shaped stirring blade, and 1,734 g of water and 60 g of 28% ammonia water were added to the flask. The pH of the liquid at this point was 11.3. Following lowering of the temperature to 5 to 10° C., 51 g of methyltrimethoxysilane (an amount that yields 4.2 parts by mass of a polymethylsilsesquioxane following the hydrolysis and condensation reaction per 100 parts by mass of the silicone elastomer spherical microparticles) was added dropwise to the flask over a period of 20 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the methyltrimethoxysilane.

The thus obtained methyltrimethoxysilane hydrolysis-condensation reaction liquid was dewatered in the same manner as example 1, yielding microparticles with good flowability. Inspection of these microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 12 μm.

With the exception of using the methylhydrogenpolysiloxane B4 instead of the methylhydrogenpolysiloxane B1, a non-sticky silicone elastomer was obtained in the same manner as example 1. Measurement of the hardness of this silicone elastomer using a type A durometer prescribed in JIS K 6253 yielded a result of 29.

With the exception of using the methylhydrogenpolysiloxane B4 instead of the methylhydrogenpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]–5.0 (g).

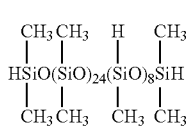
(8)

Comparative Example 2

A water dispersion of silicone elastomer microparticles was obtained in the same manner as comparative example 1, with the exceptions of replacing the 19 g of the methylhydrogenpolysiloxane B4 with 17 g of a methylhydrogenpolysiloxane B5 represented by formula (9) shown below and having a dimethylsiloxane unit content of 66.7 mol %, a molecular weight of 10,577 and a SiH group content of 0.473 mol/100 g (an amount equivalent to 1.07 SiH groups within the methylhydrogenpolysiloxane B5 per vinyl group within the methylvinylpolysiloxane A1), and altering the amount of water added immediately prior to obtaining the uniform white emulsion from 377 g to 379 g. Inspection of the shape of these silicone elastomer microparticles in the same manner as comparative example 1 revealed spherical particles, and measurement of the volume average particle diameter in the same manner as comparative example 1 yielded a result of 12 μm.

With the exceptions of using 1,161 g of the obtained water dispersion of silicone elastomer spherical microparticles as a raw material, and altering the amount of water added from 1,734 g to 1,729 g, a hydrolysis-condensation reaction and subsequent dewatering were conducted in the same manner as comparative example 1, thus forming microparticles with good flowability. During this process, the pH of the liquid upon addition of the 1,729 g of water and 60 g of 28% ammonia water was 11.3, and the amount of the polyorganosilsesquioxane following the hydrolysis-condensation reaction was 4.2 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 12 μm.

With the exception of using the methylhydrogenpolysiloxane B5 instead of the methylhydrogenpolysiloxane B1, a non-sticky silicone elastomer was obtained in the same manner as example 1. Measurement of the hardness of this silicone elastomer using a type A durometer prescribed in JIS K 6253 yielded a result of 31.

With the exception of using the methylhydrogenpolysiloxane B5 instead of the methylhydrogenpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

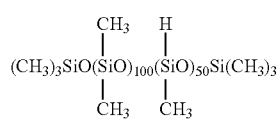

(9)

Comparative Example 3

A water dispersion of silicone elastomer microparticles was obtained in the same manner as comparative example 1, with the exceptions of replacing the 500 g of the methylvinylpolysiloxane A1 with 500 g of a methylvinylpolysiloxane A3 represented by formula (10) shown below and having a dimethylsiloxane unit content of 100 mol %, a molecular weight of 33,531 and a vinyl group content of 0.006 mol/100 g, altering the amount of the methylhydrogenpolysiloxane B4 from 19 g to 8 g (an amount equivalent to 1.11 SiH groups within the methylhydrogenpolysiloxane B4 per vinyl group within the methylvinylpolysiloxane A3), and altering the amount of water added immediately prior to obtaining the uniform white emulsion from 377 g to 388 g. Inspection of the shape of these silicone elastomer microparticles in the same manner as comparative example 1 revealed spherical particles, and measurement of the volume average particle diameter in the same manner as comparative example 1 yielded a result of 13 μm.

With the exceptions of using 886 g of the obtained water dispersion of silicone elastomer spherical microparticles as a raw material, and altering the amount of water added from 2,003 g to 1,999 g, a hydrolysis-condensation reaction and subsequent dewatering were conducted in the same manner as example 1, thus forming microparticles with good flowability. During this process, the pH of the liquid upon addition of the 1,999 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 13 μm.

With the exceptions of using the methylvinylpolysiloxane A3 instead of the methylvinylpolysiloxane A1, and using the methylhydrogenpolysiloxane B4 instead of the methylhydrogenpolysiloxane B1, a non-sticky silicone elastomer was obtained in the same manner as example 1. Measurement of the hardness of this silicone elastomer using a type A durometer prescribed in JIS K 6253 yielded a result of 21.

With the exceptions of using the methylvinylpolysiloxane A3 instead of the methylvinylpolysiloxane A1, and using the methylhydrogenpolysiloxane B4 instead of the methylhydrogenpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

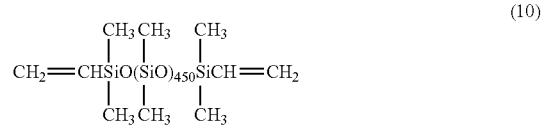

(10)

TABLE 1

| Item | | Example 1 | Example 2 | Example 3 | Comparative example 1 | Comparative example 2 | Comparative example 3 |
|---|---|---|---|---|---|---|---|
| Silicone elastomer oil absorption amount [g/1 g of silicone elastomer] | Decamethyl-cyclopentasiloxane (viscosity: 4.0 mm²/s) | 3.8 | 3.6 | 3.7 | 1.9 | 1.8 | 2.2 |
| | Dimethylpolysiloxane (viscosity: 6.0 mm²/s) | 2.4 | 2.4 | 2.5 | 1.2 | 1.1 | 1.5 |
| Microparticles oil absorption amount [g/5 g of microparticles] | Decamethyl-cyclopentasiloxane (viscosity: 4.0 mm²/s) | 27 | 29 | 26 | 16 | 15 | 17 |
| | Dimethylpolysiloxane (viscosity: 6.0 mm²/s) | 20 | 22 | 20 | 10 | 9 | 12 |

The silicone microparticles of examples 1 to 3 exhibited properties that enabled the absorption of large amounts of polymethylsiloxanes having a viscosity of not more than 10 mm²/s, which represent low-viscosity silicones, and can therefore be expected to provide a suppression effect on the greasiness, stickiness, and oily film feeling of cosmetic materials containing this type of polymethylsiloxane. In contrast, the silicone microparticles of comparative examples 1 to 3 exhibited only minimal absorption of these polymethylsiloxanes, meaning the effect mentioned above cannot be expected.

What is claimed is:

1. Silicone microparticles, comprising 100 parts by mass of silicone elastomer spherical microparticles having a volume average particle diameter within a range from 0.1 to 100 µm, and 0.5 to 25 parts by mass of a polyorganosilsesquioxane present on a surface of the silicone elastomer spherical microparticles, wherein the silicone elastomer is capable of absorbing not less than 200 parts by mass of a polymethylsiloxane having a viscosity at 25° C. of not more than 10 mm²/s per 100 parts by mass of the silicone elastomer, and the silicone elastomer is a cured product of a liquid silicone composition comprising:

(A)

(A1) an organopolysiloxane represented by an average composition formula (1) shown below:

$$R^1{}_a R^2{}_b SiO_{(4-a-b)/2} \quad (1)$$

wherein $R^1$ represents an unsubstituted or substituted monovalent hydrocarbon group of 1 to 30 carbon atoms excluding aliphatic unsaturated groups, $R^2$ represents a monovalent olefinic unsaturated group of 2 to 6 carbon atoms, and a and b are positive numbers that satisfy $0<a<3$, $0<b\leq3$, and $0.1\leq a+b\leq3$, provided that a proportion of monovalent hydrocarbon groups of 6 to 30 carbon atoms is less than 5 mol % of all $R^1$ groups, in which not less than 90 mol % of all siloxane units other than siloxane units at molecular terminals are dimethylsiloxane units represented by a formula: —(CH₃)₂SiO—, and having a molecular weight of not less than 5,000, having two monovalent olefinic unsaturated groups within each molecule, and having a monovalent olefinic unsaturated group content of not more than 0.04 mol/100 g, (A2) an organopolysiloxane represented by the average composition formula (1), in which not less than 90 mol % of all siloxane units other than siloxane units at molecular terminals are dimethylsiloxane units represented by a formula: —(CH₃)₂SiO—, and having a molecular weight of not less than 5,000, having at least three monovalent olefinic unsaturated groups within each molecule, and having a monovalent olefinic unsaturated group content of not more than 0.06 mol/100 g, or a combination of component (A1) and component (A2), (B)

(B1) an organohydrogenpolysiloxane represented by an average composition formula (2) shown below:

$$R^3{}_c H_d SiO_{(4-c-d)/2} \quad (2)$$

wherein $R^3$ represents an unsubstituted or substituted monovalent hydrocarbon group of 1 to 30 carbon atoms excluding aliphatic unsaturated groups, and c and d are positive numbers that satisfy $0<c<3$, $0<d\leq3$, and $0.1\leq c+d\leq3$, provided that a proportion of monovalent hydrocarbon groups of 6 to 30 carbon atoms is less than 5 mol % of all $R^3$ groups, in which not less than 90 mol % of all siloxane units other than siloxane units at molecular terminals are dimethylsiloxane units represented by a formula: —(CH₃)₂SiO—, and having a molecular weight of not less than 5,000, having two hydrogen atoms bonded to silicon atoms within each molecule, and having a silicon atom-bonded hydrogen atom content of not more than 0.04 mol/100 g, (B2) an organohydrogenpolysiloxane represented by the average composition formula (2), in which not less than 90 mol % of all siloxane units other than siloxane units at molecular terminals are dimethylsiloxane units represented by a formula: —(CH₃)₂SiO—, and having a molecular weight of not less than 5,000, having at least three hydrogen atoms bonded to silicon atoms within each molecule, and having a silicon atom-bonded hydrogen atom content of not more than 0.06 mol/100 g, or a combination of component (B1) and component (B2), in an amount that yields from 0.5 to 2 hydrogen atoms bonded to silicon atoms within component (B) per monovalent olefinic unsaturated group within component (A), and (C) a platinum group metal-based catalyst, provided that when component (A) is component (A1), component (B) is either component (B2) or a combination of component (B1) and component (B2).

2. The silicone microparticles according to claim 1, wherein a monovalent olefinic unsaturated group content within component (A1) is not more than 0.02 mol/100 g.

3. The silicone microparticles according to claim 1, wherein a monovalent olefinic unsaturated group content within component (A2) is not more than 0.04 mol/100 g.

4. The silicone microparticles according to claim 1, wherein a silicon atom-bonded hydrogen atom content within component (B1) is not more than 0.02 mol/100 g.

5. The silicone microparticles according to claim 1, wherein a silicon atom-bonded hydrogen atom content within component (B2) is not more than 0.04 mol/100 g.

6. The silicone microparticles according to claim 1, wherein a rubber hardness of the silicone elastomer, measured using a type A durometer prescribed in JIS K 6253, is within a range from 5 to 90.

7. The silicone microparticles according to claim 1, wherein the polyorganosilsesquioxane comprises units represented by a formula $R^4 SiO_{3/2}$, wherein $R^4$ represents an unsubstituted or substituted monovalent hydrocarbon group of 1 to 20 carbon atoms.

8. The silicone microparticles according to claim 7, wherein not less than 50 mol % of all $R^4$ groups within the polyorganosilsesquioxane are methyl groups.

9. A method of producing the silicone microparticles defined in claim 1, the method comprising:

hydrolyzing and condensing an organotrialkoxysilane in a water medium, in presence of silicone elastomer spherical microparticles having a volume average particle diameter within a range from 0.1 to 100 µm and an alkaline material, thereby coating a surface of the silicone elastomer spherical microparticles with a polyorganosilsesquioxane.

10. The method according to claim 9, wherein the organotrialkoxysilane is represented by a formula $R^4 Si(OR^5)_3$, wherein $R^4$ represents an unsubstituted or substituted monovalent hydrocarbon group of 1 to 20 carbon atoms, and $R^5$ represents an unsubstituted monovalent hydrocarbon group of 1 to 6 carbon atoms.

11. A method comprising:

contacting a polymethylsiloxane having a viscosity at 25° C. of not more than 10 mm²/s with the silicone microparticles defined in claim 1, thereby absorbing the polymethylsiloxane into the silicone microparticles.

12. The silicone microparticles according to claim 1, wherein, for each of organopolysiloxane (A1) and (A2) and for each of organohydrogenpolysiloxane (B1) and (B2), not less than 95 mol % of all siloxane units thereof other than siloxane units at molecular terminals are dimethylsiloxane units represented by —(CH$_3$)$_2$SiO—.

13. The silicone microparticles according to claim 1, wherein the platinum group metal-based catalyst is present in an amount of from 0.1 to 500 ppm relative to the total mass of the composition and comprises at least one member selected from the group consisting of platinum; rhodium; palladium; a platinum chloride; a chloroplatinic acid; H$_2$PtCl$_4$.kH$_2$O; H$_2$PtCl$_6$.kH$_2$O; NaHPtCl$_6$.kH$_2$O; KHPtCl$_6$.kH$_2$O; Na$_2$PtCl$_6$.kH$_2$O; K$_2$PtCl$_4$.kH$_2$O; PtCl$_4$.kH$_2$O; PtCl$_2$; Na$_2$HPtCl$_4$.kH$_2$O; an alcohol-modified chloroplatinic acid; a complex of chloroplatinic acid and an olefin; platinum black or palladium supported on a carrier selected from the group consisting of alumina, silica and carbon; a rhodium-olefin complex; chlorotris(triphenylphosphine) rhodium; and a complex of a platinum chloride, a chloroplatinic acid or a chloroplatinate with a vinyl group-containing siloxane, and wherein k represents an integer of 0 to 6.

14. The silicone microparticles according to claim 1, wherein component (A) of the liquid silicone composition comprises at least one member selected from the group consisting of

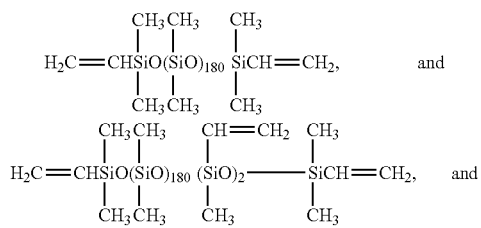

component (B) of the liquid silicone composition comprises at least one member selected from the group consisting of

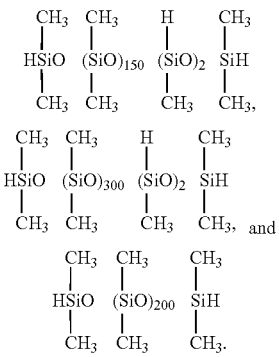

15. The silicone microparticles according to claim 1, wherein a monovalent olefinic unsaturated group content within component (A1) is from 0.001 mol/100 g to 0.02 mol/100 g.

16. The silicone microparticles according to claim 1, wherein a monovalent olefinic unsaturated group content within component (A2) is from 0.0015 mol/100 g to 0.04 mol/100 g.

17. The silicone microparticles according to claim 1, wherein a silicon atom-bonded hydrogen atom content within component (B1) is from 0.001 mol/100 g to 0.02 mol/100 g.

18. The silicone microparticles according to claim 1, wherein a silicon atom-bonded hydrogen atom content within component (B2) is from 0.0015 mol/100 g to 0.04 mol/100 g.

19. The silicone microparticles according to claim 1, wherein the polyorganosilsesquioxane is present on the surface of the silicone elastomer spherical microparticles in the form of a coating, and wherein gaps are present in the coating.

* * * * *